United States Patent [19]
Tarczynski et al.

[11] Patent Number: 6,080,913
[45] Date of Patent: Jun. 27, 2000

[54] BINARY METHODS OF INCREASING ACCUMULATION OF ESSENTIAL AMINO ACIDS IN SEEDS

[75] Inventors: Mitchell C. Tarczynski, West Des Moines, Iowa; Paul E. Staswick, Lincoln, Nebr.

[73] Assignee: Pioneer Hi-Bred International, Inc., Des Moines, Iowa

[21] Appl. No.: 08/719,500

[22] Filed: Sep. 25, 1996

[51] Int. Cl.[7] .............................. A01H 5/00; A01H 5/10; C12N 15/29; C12N 5/04

[52] U.S. Cl. .......................... 800/298; 800/278; 800/282; 800/284; 800/287; 800/317.3; 800/322; 536/23.1; 536/23.6; 435/414; 435/415; 435/426; 435/428

[58] Field of Search ................................... 800/298, 278, 800/287, 282, 284, 317.3, 322; 536/23.1, 23.6; 435/69.1, 414, 415, 426, 428

[56] References Cited

U.S. PATENT DOCUMENTS

| | | | |
|---|---|---|---|
| 5,258,300 | 11/1993 | Glassman et al. | 435/240.4 |
| 5,487,991 | 1/1996 | Vandekerckhove et al. | 435/172.3 |
| 5,633,436 | 5/1997 | Wandelt | 800/205 |

FOREIGN PATENT DOCUMENTS

| | | |
|---|---|---|
| 485970 | 5/1992 | European Pat. Off. . |
| 40 13 144 A1 | 10/1991 | Germany . |
| WO 92/14822 | 9/1992 | WIPO . |
| WO 94/10319 | 5/1994 | WIPO . |
| WO 94/21805 | 9/1994 | WIPO . |
| WO 96/38563 | 12/1996 | WIPO . |
| WO 97/28247 | 8/1997 | WIPO . |

OTHER PUBLICATIONS

Staswick, Paul E., "Preferential Loss of an Abundant Storage Protein from Soybean Pods during Seed Development", *Plant Physiology*, vol. 90, pp. 1252–1255, 1989.

Leopold et al (Eds). Flowering . in 'Plant Growth and Dvelopment', pp. 318–321, McGraw–Hill Inc., New–York, 1975.

Burow, et al. "Suppression of Phaseolin and Lectin in Seeds of Common Bean, *Phaseolus vulgaris* L.: Increased Accumulation of 54 kDa Polypeptides is not Associated with Higher Seed Methionine Concentrations"; *Mol. Gen. Genet.*; vol. 241; pp. 431–439; (1993).

Karchi, et al. "Seed–specific Expression of a Bacterial Desensitized Aspartate Kinase Increases the Production of Seed Threonine and Methionine in Transgenic Tobacco"; *The Plant Journal*; vol. 3(5); pp. 721–727; (1993).

Thompson, et al. "Structural Elements Regulating Zein Gene Expression"; *BioEssays*; vol. 10(4); pp. 108–113; (1989).

Bray, et al. "Expression of the β–subunit of β–conglycinin in Seeds of Transgenic Plants"; *Planta*; vol. 172; pp. 364–370; (1987).

Pedersen, et al. "Cloning and Sequence Analysis Reveal Structural Variation Among Related Zein Genes in Maize"; *Cell*; vol. 29; pp. 1015–1026; (1982).

Kirihara, et al. "Differential Expression of a Gene for a Methionine–rich Storage Protein in Maize"; *Mol. Gen. Genet.*; vol. 211; pp. 477–484; (1988).

Coulter, et al. "Chracterization of a Small Sulphur–Rich Storage Albumin in Seeds of Alfalfa (*Medicago sativa* L.)"; *J. Experimental Botany*; vol. 41 (233); pp. 1541–1547; (1990).

Altenbach, et al. "Cloning and Sequence Analysis of a cDNA encoding a Brazil Nut Protein Exceptionally Rich in Methionine"; *Plant Molecular Biology*; vol. 8; pp. 239–250; (1987).

Lilley, et al. "Isolation and Primary Structure for a Novel, Methionine–rich Protein from Sunflowerseeds (*Helianthus annus.* L.)" *Proceedings of the World Congress on Vegetable Protein Utilization in Human Foods and Animal Feedstuffs*:; pp., 497–502; (1989).

Kortt, et al. "Low Molecular Weight Albumins from Sunflower Seed: Identification of a Methionine–rich Albumin"; *Phytochemistry*; vol. 29(9); 2805–2810; (1990).

Masumura, et al. "cDNA Cloning of an mRNA Encoding a Sulfur–rich 10 kDa Prolamin Polypeptide in Rice Seeds"; *Plant Molecular Biology*; vol. 12, pp. 123–130; (1989).

Shewry et al. "Seed Storage Proteins: Structures and Biosynthesis"; *The Plant Cell*; vol. 7; pp. 945–956; (1995).

Phillips, et al., "Induction and Development of Somatic Embryos from Cell Suspension Cultures of Soybean"; *Plant Cell Tissue Organ Culture*; vol. 1; pp. 123–129; (1981).

Paterson, et al., "Regeneration of *Helianthus annuus* Inbred Plants from Callus"; *Plant Sci.*; vol. 42; pp. 125–132; (1985).

Wright, et al., "Regeneration of Soybean (*Glycine max* L. Merr.) from Cultured Primary Leaf Tissue"; *Plant Cell Reports*; vol. 6; pp. 83–89; (1987).

Barwale, et al., "Plant Regeneration from Callus Cultures of Several Soybean Genotypes via Embryogenesis and Organogenesis"; *Planta*; vol. 167; pp. 473–481; (1986).

Florack, et al., "Expression of Biologically Active Hordothionins in Tobacco. Effects of Pre– and Pro–sequences at the Amino and Carboxyl Termini of the Hordothionin Precursor on Mature Protein Expression and Sorting"; *Plant Mol. Biol.*; vol. 24; pp. 83–96; (1994).

Rhee, et al., "Nucleotide Sequence of a Soybean Vegetative Storage Protein vspA Gene"; *Plant Physiol.*; vol. 98; pp. 792–793; (1992).

(List continued on next page.)

*Primary Examiner*—Robert A. Wax
*Assistant Examiner*—Tekchand Saidha
*Attorney, Agent, or Firm*—Pioneer Hi-Bred International, Inc.

[57] ABSTRACT

The present invention provides methods for genetically modifying plants to increase the levels of essential amino acids in seed. The present methods involve a combination of:

a) providing an increased reservoir or source of a target amino acid population in vegetative tissue; with b) a complementary protein sink.

22 Claims, No Drawings

OTHER PUBLICATIONS

Kollipara, et al., "Characterization of Trypsin and Chymotrypsin Inhibitors in the Wild Perennial Glycine Species"; *J. Agric. Food Chem.*; vol. 40; pp. 2356–2363; (1992).

Geiger, Reinhard; "Chymotrypsin"; *Methods of Enzymatic Analysis*; pp. 99–109; (1984).

Sengupta–Gopalan, et al., "Developmentally Regulated Expression of the Bean β–Phaseolin Gene in Tobacco Seed"; *Proc. Nat'l. Acad. Sci.*; vol. 82; pp. 3320–3324; (1985).

Wandelt, et al., "Vicilin with Carboxy–terminal KDEL is Retained in the Endoplasmic Reticulum and Accumulates to High Levels in the Leaves of Transgenic Plants"; *The Plant Journal*; vol. 2(2); pp. 181–192; (1992).

Armstrong, et al., "Development and Availability of Germplasm with High Type II Culture Formation Response"; *Maize Genetics Coop. News*; vol. 65; pp. 92–93; (1991).

Chu, et al., "Establishment of an Efficient Medium for Anther Culture of Rice Through Comparative Experiments on the Nitrogen Sources"; *Sci. Sin.*; vol. 18(5); pp. 659–668; (1975).

Eriksson, Tage; "Studies on the Growth Requirements and Growth Measurements of Cell Cultures of *Haplopappus gracilis*"; *Physiol. Plant.*; vol. 18; pp. 976–993; (1965).

Murashinge, et al., "A Revised Medium for Rapid Growth and Bio Assays with Tobacco Tissue Cultures"; *Physiol. Plant.*; vol. 15, pp. 473–497; (1962).

Wallace, et al., "New Methods for Extraction and Quantitation of Zeins Reveal a High Content of γ–Zein in Modified Opaque–2 Maize"; *Plant Physiol.*; vol. 92; pp. 191–196; (1990).

Laemmli, U.K., "Cleavage of Structural Proteins During the Assembly of the Head of Bacteriophage T4"; *Nature*; vol. 227; pp. 680–685; (1970).

Lending, et al., "Structure of Maize Protein Bodies and Immunocytochemical Localization of Zeins"; *Protoplasma*; vol. 143; pp. 51–62; (1988).

Knecht, et al., "Visualization of Antigenic Proteins on Western Blots"; *Anal. Biochem.*; vol. 136; pp. 180–184; (1984).

BINARY METHODS OF INCREASING ACCUMULATION OF ESSENTIAL AMINO ACIDS IN SEEDS

FIELD OF THE INVENTION

The present invention relates to the field of animal nutrition. Specifically, the present invention relates to methods of enhancing the nutritional content of seeds used in animal feed.

BACKGROUND

Feed formulations are required to provide animals with essential nutrients critical to growth. However, crop plants are generally rendered food sources of poor nutritional quality because they contain low proportions of several amino acids which are essential for, but cannot be synthesized by animals. For example, soybean meal in deficient in the essential sulfur-containing amino acids, methionine and cysteine, because the most abundant proteins accumulated in soybean seeds are relatively low in these amino acids. Supplementation of animal feeds to bring the levels of essential amino acids up to that required constitutes significant added expense.

For many years, researchers have attempted to improve the balance of essential amino acids in the seed proteins of important crops through breeding programs. Efforts utilizing classical breeding and mutant selection have met with limited success, probably because little variability exists in seed amino acid content. While there have been recent reports of the selection of arabidopsis mutants that overaccumulate high levels of free methionine, because free methionine represents only a small fraction of total methionine, the reported increases in free methionine translate to insignificant changes in total methionine content.

As more becomes known about seed storage proteins and the expression of the genes which encode these proteins, and as transformation systems are developed for a greater variety of plants, molecular approaches for improving the nutritional quality of seed proteins can provide alternatives to the more conventional approaches. Thus, specific amino acid levels can be enhanced in a given crop via biotechnology.

One alternative method is to express a heterologous protein of favorable amino acid composition at levels sufficient to obviate or significantly reduce feed supplementation. For this purpose, a number of seed proteins rich in sulfur amino acids have been identified. A key to good expression of such proteins involves efficient expression cassettes with seed specific promoters. Not only must the gene-controlling regions direct the synthesis of high levels of mRNA, the mRNA must be translated into stable protein.

Essential amino acids, needed for animal nutrition but often limited in crop plants, include methionine, threonine, cysteine and lysine. Attempts to increase the levels of these free amino acids by breeding, mutant selection and/or changing the composition of the storage proteins accumulated in crop plants have met with minimal success. Usually, the expression of the transgenic storage protein does not result in sufficient increase in the total seed amino acid. The phaseolin-promoted Brazil nut 2S expression cassette is an example of an effective chimeric seed-specific gene. However, even though Brazil nut protein increases the amount of total methionine and bound methionine, thereby improving nutritional value, there appears to be a threshold limitation as to the total amount of methionine that is accumulated in the seeds. The seeds remain insufficient as sources of methionine and significant methionine supplementation is required in diets utilizing the above soybeans.

An alternative to the enhancement of specific amino acid levels by altering the levels of proteins containing the desired amino acid is modification of amino acid biosynthesis. Recombinant DNA and gene transfer technologies have been applied to alter enzyme activity catalyzing key steps in the amino acid biosynthetic pathway. Glassman, U.S. Pat. No. 5,258,300; Galili, et al., European Patent Application No. 485970; (1992); incorporated herein in its entirety. However, modification of the amino acid levels in seeds is not always correlated with changes in the level of proteins that incorporate those amino acids. Burrow, et al., *Mol. Gen. Genet.*; Vol. 241; pp. 431–439; (1993); incorporated herein in its entirety by reference. Increases in free lysine levels in leaves and seeds have been obtained by selection for DHDPS mutants or by expressing the *E. coli* DHDPS in plants. However, since the level of free amino acids in seeds, in general, is only a minor fraction of the total amino acid content, these increases have been insufficient to significantly increase the total amino acid content of seed.

The lysC gene is a mutant bacterial aspartate kinase which is desensitized to feedback inhibition by lysine and threonine. Expression of this gene results in an increase in the level of lysine and threonine biosynthesis. However, expression of this gene with seed-specific expression cassettes has resulted in only a 6–7% increase in the level of total threonine or methionine in the seed. See Karchi, et al., *The Plant J.*; Vol. 3; pp. 721–7; (1993); incorporated herein in its entirety by reference. Thus, there is minimal impact on the nutritional value of seeds, and supplementation with essential amino acids is still required.

Based on the foregoing, there exists a need for methods of increasing the levels of essential amino acids in seeds of plants. As can be seen from the prior art, previous approaches have led to insufficient increases in the levels of both free and bound amino acids to significantly enhance the nutritional content of the feed. There exists a need to significantly increase the levels of the essential amino acids in seeds.

It is therefore an object of the present invention to provide methods for genetically modifying plants to increase the levels of essential amino acids in the seeds of such plants.

It is a further object of the present invention to provide seeds for food and/or feed with higher levels of essential amino acids than the wild type species of the same seeds.

It is a further object of the present invention to provide seeds for food and/or feed such that the level of the essential amino acids is increased, thus obviating or reducing the need for feed supplementation.

SUMMARY

The present invention provides methods for genetically modifying plants to increase the levels of the essential amino acids in seeds. The present methods involve a combination of: a) providing an increased reservoir or source of a target amino acid population in vegetative tissue; with b) a complementary protein sink, the result of which is an unexpectedly increased accumulation of the target amino acids in seeds.

The present methods involve transforming plants with vegetative or storage-organ specific genes encoding target amino acid sequences. A first transgene encoding a target amino acid sequence is expressed in a non-seed organ or tissue, and the target amino acid encoded by the transgene accumulates in the protein of these organs.

In a preferred embodiment of the present invention, the plant may contain a second, seed-specific transgene which leads to the synthesis and accumulation of proteins enriched for a target amino acid. The engineered protein, which accumulates in organs other than seed, is degraded as the seed develops and serves as an enriched source of the target amino acid which may otherwise be limiting during seed development.

Thus, in the present binary system, as the seed develops, there is additional accumulation of the target amino acid as a result of the expression of the first transgene in a given organ and the subsequent availability of the target amino acid derived from the source protein.

DETAILED DESCRIPTION

It has been unexpectedly discovered that the seeds of plants may have a diminished capacity to reduce and/or assimilate nitrogen and/or sulfur needed for amino acid biosynthesis. It is also believed that nitrogen and/or sulfur is compartmentalized such that it cannot be reduced and/or assimilated. The seeds therefore rely on other tissues or organs of the plant as sources for their amino acid needs. Amino acid from the source is delivered to developing seeds and then incorporated into protein, virtually eliminating the limitation.

As used herein, "protein sink" means a stably accumulated protein that may contain abundant amounts of a target amino acid.

As used herein, "source" or "protein source" means free amino acid available for protein biosynthesis.

As used herein, "free amino acid" means an amino acid that is unmodified or the direct result of its synthesis.

As used herein, "target amino acid" means an amino acid that is to be overproduced and/or overaccumulated in seed.

As used herein, "selected protein" means a protein, or its genetic equivalent, that contains elevated levels of target amino acid.

As used herein, "higher yield" means increased quantity of protein in seed and/or increased quantity of protein per acre and/or increased quantity of dry matter per acre.

As used herein, "vegetative storage protein" means protein which accumulates in the vegetative matter of the plant.

As used herein, "genetically modified" means a plant cell stably incorporating a nucleic acid construct introduced by transformation methods. The term "wild type" refers to an untransformed plant or plant cell.

As used herein, "altered composition of a vegetative storage protein" means an altered amino acid composition of a vegetative storage protein.

As used herein, "altered quantity of a vegetative storage protein" means a change in the level of accumulation of a vegetative storage protein.

Preferred plants that produce seeds wherein protein content may be improved by this method include, but are not limited to: soybean, canola, corn, sunflower, wheat, barley, oats, millet, rice, sorghum, and rye. More preferred plants are soybean, corn, sunflower and canola. In the practice of the present invention, the most preferred plant seed is *Glycine max*. The seeds may be used directly as feed or food, or further processing may occur.

In accordance with this invention, there is provided a simple, rapid, and reliable process for the production of transgenic plants with increased accumulation of essential amino acids in the resulting seeds. The method is genotype independent and shows a substantial, unexpected improvement over previously used systems.

As used herein "genotype independent" means that beneficial results are not dependent on a particular genotype.

The present invention involves expression of a first transgene, coding for a target amino acid sequence in an organ or tissue, followed by accumulation of the target amino acid in the organ or tissue. As the seed develops, the protein degrades and serves as a source of the amino acid which may otherwise be a limitation during seed development.

In a preferred embodiment of the present invention, a second transgene is expressed. The second transgene is seed specific and, before and during seed development, leads to the synthesis and accumulation of the same target amino acid in seed as that selected for the first transgene.

The present invention also involves expression of a first transgene, coding for a protein enriched in a target amino acid, in an organ or tissue followed by accumulation of the protein in the organ or tissue. As the seed develops, the protein degrades and serves as a source of the amino acid which may otherwise be a limitation during seed development. Thus, as seed development occurs, the seed accumulates protein enriched in the target amino acid because of the expression of the first transgene in a given tissue or organ and the subsequent availability of the target amino acid derived from the source protein.

In a preferred embodiment of the present invention, a second, seed-specific transgene is also expressed. Before and/or during seed development, the second transgene leads to the synthesis and accumulation of a seed protein enriched in a target amino acid that may be the same as that selected for the first transgene or a different target amino acid.

The target amino acid includes, but is not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. Preferably, the target amino acid includes methionine, lysine, threonine, isoleucine, cysteine, arginine, histidine, leucine, phenylalanine, valine and tryptophan. More preferably, the target amino acid includes methionine, lysine, threonine, isoleucine and cysteine. More preferably, the target amino acid is lysine or methionine. Also preferably, the target amino acid is methionine.

As used herein "enriched" means containing a higher percentage of amino acid than the average protein, preferably 20%, more preferably 50%, even more preferably 200%, more preferably still 500%, and most preferably 750% greater amino acid than the average protein.

The transgene contains a promoter/transit peptide, a high target amino acid structural gene and a terminator. Such promoters, transit peptides, structural genes and terminators are well known to the skilled artisan. Expression of the gene sequence is under the control of a promoter, including constitutive or inducible promoters. Examples of suitable promoters include, but are not limited to, the promoter for the small subunit of ribulose-1,5-bis-phosphate carboxylase, soybean vsp promoters, promoters from tumor-inducing plasmids of *Agrobacterium tumefaciens*, such as the nopaline synthase and octopine synthase promoters, and viral promoters such as the cauliflower mosaic virus (CaMV) 19S and 35S promoters or the figwort mosaic virus 35S promoter.

When seed-specific expression is desired, "seed-specific" promoters are preferred. As used herein, "seed-specific" promoters are promoters that drive high expression of a structural gene in seed tissue where control of genes that are involved in seed metabolism is desired, and little or no expression in other parts of the plant occurs. Examples of known seed-specific promoters include, but are not limited to, the promoters of seed storage proteins which express these proteins in seeds in a highly regulated manner. (See e.g., Thompson, et al., *BioEssays*; Vol. 10; pp. 108–113; (1989); incorporated herein in its entirety by reference); the soybean promoter of β-conglycinin (also known as the 7S protein) which drives seed-directed transcription (See e.g. Bray, *Planta*; Vol. 172; pp. 364; (1987); incorporated herein in its entirety by reference); and promoters from the zein genes of maize endosperm (See e.g. Pedersen, et al., *Cell*; Vol. 29; pp. 1015; (1982); incorporated herein in its entirety by reference). Several promoters for expression of proteins in seeds of dicotyledonous plants of particular use include but are not limited to bean β-phaseolin, napin, β-conglycinin and soybean lectin. For monocotyledonous plants, maize 15 kD zein, 22 kD zein, γ-zein, waxy, shrunken 1, globulin 1 and shrunken 2 promoters are useful. A particularly preferred promoter for soybean is the β-phaseolin promoter. Those skilled in the art will recognize other promoters as well that will provide constructs for increased levels of the preselected protein in the plant chosen for transformation.

When vegetative/storage organ or tissue-specific expression is desired, preferred promoters include, but are not limited to vspA, vspB, rubisco activase, ferredoxin, rubisco small subunit and chlorophyll AB binding protein promoters.

The structural gene with a high level of a target amino acid includes but is not limited to the gene for a rice (*Oryza sativa* L) 10 kDa or 16 kDa prolamin; a sunflower (*Helianthus annus* L) 2S albumin protein, Brazil nut 2S albumin protein, a soybean seed storage protein, 10 kDa zein protein, thionin and 2S albumin from alfalfa. See e.g. *Mol. Gen. Genet.*; Vol. 211; pp. 477–484; (1988); *J. Exp. Bot.*; Vol. 41; pp. 1541–1547; (1990); Altenbach, et al., *Plant Mol. Biol.*; Vol. 8; pp. 239–250; (1987); all incorporated herein in their entirety by reference.

Sulfur-rich sunflower 2S albumin proteins are described in Lilley, et al., "Isolation and Primary Structure for a Novel Methionine-rich Protein from Sunflower Seeds (*Helianthus annus*. L)", *Proceedings of the World Congress on Vegetable Protein Utilization in Human Foods and Animal Feedstuffs*; pp. 497–502; (1989); and by Kortt, et al., *Phytochemistry*; Vol. 29; pp. 2805; (1990); both incorporated herein in their entirety by reference. Eight proteins, denoted sunflower albumins ("SFA") 1 to 8, are identified in the 2S albumin fraction. Two of these, SFA-7 and SFA-8, are sulfur rich. SFA-8 is present in greater amounts than SFA-7, and for this reason is preferred.

Matsumura, et al., *Plant Molec. Biol.*; Vol. 12; p. 123; (1989); incorporated herein in its entirety by reference, describe three prolamine polypeptides isolated from rice seeds, denoted "10 kDa", "13 kDa" and "16 kDa" proteins which are said to be sulfur-rich. A full length clone for the 10 kDa prolamin is also described, and this embodiment is a preferred one.

A soybean seed storage protein is described in Shewry, et al., *The Plant Cell*; Vol. 7(7); pp. 945–956; (1995); incorporated herein in its entirety by reference. A preferred embodiment is a gene encoding a soybean albumin.

As used herein with respect to a protein, the term "heterologous" means that the gene or gene fragment encoding the protein is obtained from one or more sources other than the genome of the species of plant within which it is ultimately expressed. The source can be natural, e.g. the gene can be obtained from another source of living matter, such as bacteria, yeast, fungi and the like, or a different species of plant. The source can also be synthetic, e.g. the gene or gene fragment can be prepared in vitro by chemical synthesis. For the purposes of this invention, proteins can be heterologous, synthetic or endogenous. As used herein, "endogenous" protein refers to the native protein normally found in its natural location in the plant.

As used herein with respect to a preselected protein, the term "expresses" means that the gene encoding this protein is stably incorporated into the genome of the cells, so that the product encoded by the gene, e.g., a methionine-rich protein such as Brazil nut protein (BNP), is produced within the cells.

The properties of the nucleic acid sequences encoding the preselected protein may vary and the preferred embodiment describes a number of features which may be advantageous. However, a person skilled in the art will recognize other options and be able to select a particular construct and vector to introduce the sequence into the cell and produce expression of the protein. A skilled artisan can also construct an expression cassette adequate for expression of the preselected protein in the chosen cellular system with no undue experimentation. The heart of the present invention is the level of the target amino acid; therefore, additional copies of the nucleic acid sequence will normally result in increased synthesis of the amino acid.

The skilled artisan will recognize that the choice of a preselected protein will be based on the amino acid composition of the protein and its ability to accumulate in seeds. This includes all classes of seed storage proteins; the 2S, 7S, and 11S proteins with or without modification to increase the content of the designated amino acid in the protein. The amino acid is chosen for its nutritional value to produce a value-added trait to the plant.

As used herein, "plant" refers to either a whole plant, a plant part, a plant cell, or a group of plant cells. The class of plants which can be used in the method of the invention is generally as broad as the class of seed-bearing higher plants amenable to transformation techniques, including both monocotyledonous and dicotyledonous plants. The transformation of the plants in accordance with the invention may be carried out in essentially any of the various ways known to those skilled in the art of plant molecular biology. These include but are not limited to particle bombardment, microinjection, electroporation, and Agrobacterium-mediated DNA transfer.

Following transformation, regeneration will normally be involved in obtaining a whole plant from the transformation process. Techniques for regenerating plants from tissue culture, such as transformed protoplasts or callus cell lines, are known in the art. See, e.g., Phillips, et al., *Plant Cell Tissue Organ* Culture; Vol. 1; p. 123; (1981); Patterson, KE. and N. P. Everett, *Plant Sci.*; Vol. 42; pp. 125–132; (1985); Wright, et al., *Plant Cell Reports*; Vol. 6; pp. 83–89; (1987); Barwale, et al., *Planta*; Vol. 167; p. 473; (1986); all incorporated herein in their entirety by reference. The selection of an appropriate method is within the skill of the art.

The expression vectors utilized herein with respect to soybean are demonstrably capable of operation in cells of many dicotyledonous plants both in tissue culture and in whole plants. The invention disclosed herein is thus operable in dicotyledonous species to transform individual plant cells and to achieve full, intact plants in dicot plant species which can be regenerated from transformed plant calli and which express preselected seed proteins. For those species not presently regenerable, the present invention is fully operable when the techniques for such regeneration become developed.

In addition, chimeric expression vectors involving seed proteins are also known and have been described in the literature which have been demonstrated to be operable in cells of monocots, at least in tissue culture. It is reasonable then to expect that these vectors will also be operable in whole monocot plants when the techniques for regenerating these plants are perfected so that any preselected seed protein can be expressed in any monocotyledonous plant seed. The present invention is thus applicable to monocots as well as to dicots.

An example of a monocot embodiment of the present invention would be the introduction of a high lysine derivative of α-hordothionin into a maize cell to increase the lysine content of the seed.

Thionins are small antimicrobial proteins present in the endosperm of barley, wheat, and other plant species. Florack, et al., *Plant Mol. Biol.*; Vol. 24; pp. 83–96; (1994); incorporated herein in its entirety by reference. Native α-hordothionin is rich in arginine and lysine residues, containing five residues (10%) of each. Several derivatives of this protein have been made in which other amino acids were replaced with lysine to produce a compound less toxic to fungi and significantly more enriched with lysine (29% lysine).

In the present invention, the first transgene is preferably expressed in the root, leaf, stems, pod, mesophyll, palisade, cortex, bundle sheath, paraveinal mesophyll or epidermis. Preferably, the first transgene is expressed in the leaf, pod, stem, paraveinal mesophyll or bundle sheath. Most preferably, expression occurs in the paraveinal mesophyll.

The present invention encompasses an embodiment in which:

a) a first transgene encoding a target amino acid sequence is expressed in an organ or tissue of a first plant;

b) a second transgene which leads to the synthesis and accumulation of a target amino acid sequence in seed is expressed in a second plant; and c) the two plants are crossed to achieve an effect of targeting both an organ or tissue other than seed and the seed of the progeny.

The foregoing is one description of the scope of the invention and a skilled artisan will recognize many other examples of plant improvement to which the invention can be applied.

The present invention can be better understood by reference to the following more detailed examples which illustrate its various applications, but are in no way intended to limit the scope thereof.

EXAMPLES

I. Expression of Sunflower cDNA in Soybean Vegetative Organs

A) Construction of Expression Vector

Full length cDNA clone for the sunflower SFA-8 protein is obtained by RT-PCR with first strand cDNA as template and gene-specific primers designed against published sequences. See Matsumura, et al. and Lilley, et al., supra. The resulting PCR product is subcloned into pBluescript containing a PINII terminator sequence and confirmed by sequence analysis. A genomic clone containing the vspA promoter, transit sequence and vspA structural gene is known and published. See Rhee, et al., "Nucleotide Sequence of a Soybean Vegetative Storage Protein vspA Gene"; *Plant Physiol.*; Vol. 98; pp. 792-793; (1992); incorporated herein in its entirety by reference. An EcoRI-HindIII fragment from the 5' end of the vspA gene is subcloned into pBluescript and contains the vspA promoter, transit sequence and a portion of the vspA structural gene. A BssHII restriction site is incorporated at the position shown in FIG. I by silent, site-directed mutagenesis, and this is confirmed by sequencing. The EcoRI-BssHII fragment is excised and subcloned into pSE280, creating a vector that contains the vspA promoter and transit sequence. The sunflower SFA-8, cDNA and PINII terminator sequence (in pBluescript) is excised and the 5' end is ligated in frame to the 3' end of the vector containing the vspA promoter and transit sequence. This expression construct which contains the vspA promoter, transit sequence and full-length sunflower cDNA and PINII terminator sequence, is then transferred to the binary vector pARC12, a vector which contains the NPTII selectable marker for plant selection. The resulting binary vector for SFA-8 is transformed into *Agrobacterium tumefaciens* strain LBA4404 by a freeze-thaw method known in the art.

B) Explant Preparation, Transformation and Transgenic Plant Recovery

Seeds of soybean (*Glycine max*), var. PHI9341, are surface sterilized by exposure to chlorine gas evolved in a glass bell jar. Gas is produced by adding 3.5 ml hydrochloric acid (34–37% w/w). Exposure is for 16–20 hours in a container approximately one cubic foot in volume. Surface sterilized seed is stored in petri dishes at room temperature. Seed is germinated by plating of 1/10 strength agar solidified medium according to Gamborg (B5 basal medium with minimal organics, Sigma Chemical co., Cat. No. G5893, 0.32 gm/L; sucrose, 0.2% w/v and 2-[N-morpholino] ethanesulfonic acid] (MES), 3.0 mM without plant growth regulators and culturing at 28° C. with a 16 hour day length and cool white fluorescent illumination of approximately 20 $\mu Em^2 S^1$. After three or four days, seed is prepared for co-cultivation. The seed coat is removed and the elongating radical is removed 3–mm below the cotyledons. Ten prepared seed are held in each of several petri dishes.

Overnight cultures of *A. tumefaciens* LBA4404 harboring the expression construct, are grown to log phase in Minimal A medium containing tetracycline, 1.0 μg/ml. Cultures are pooled and an optical density at 550 nm is measured. An amount of culture sufficient to collect upon sedimentation between 1.0 and $2.0 \times 10^{10}$ cells, where O.D. 550 1.0=1.4× $10^9$ cells/ml, is placed in a 15 ml conical centrifuge tube, and spun down at 6000 g for 10 minutes. After centrifugation the supernatant is decanted and the tubes are held at room temperature until inoculum is needed, but not longer than one hour.

Inoculations are conducted in batches such that each plate of seed is treated with a newly resuspended pellet of *A. tumefaciens* harboring the construct. One at a time the pellets are resuspended in 20 ml inoculation medium. Inoculation medium consists of B5 salts (B5893), 3.2 gm/L; sucrose, 2.0% w/v; BAP, 44 μM; and indolebutyric acid (IBA), 0.5 μM. Acetosyringone (AS), 100 μM is added and the medium is buffered to pH 5.5 with MES, 10 mM.

The mixture is resuspended by vortexing and the inoculum is poured into a petri dish containing prepared seed and the cotyledonary nodes are macerated with a surgical blade. This is accomplished by dividing seed in half by longitudinal section through the shoot apex, preserving the two whole cotyledons. The two halves of the shoot apex are broken off at their respective cotyledons by prying them away with a surgical blade. The cotyledonary node is then macerated with the surgical blade by repeated scoring along the axis of symmetry. Care is taken not to cut entirely through the explant to the adaxial side. Twenty explants are prepared in roughly five minutes and then incubated for 30 minutes at room temperature without agitation. Additional plates are prepared during this time. After 30 minutes the explants are transferred to plates of the same medium solidified with Gelrite (Merck & Co., Inc.), 0.2% w/v. Explants are embedded with the adaxial side up and level with the surface of the medium and cultured at 22° C. for three days under cool white fluorescent light. Approximately 20 $\mu Em^2S^1$.

After three days the explants are moved to liquid counterselection medium. Counterselection medium consists of B4 salts (G5893), 3.2 gm/L; sucrose, 2.0% w/v; BAP, 5.0 $\mu M$; IBA, 0.5 $\mu M$; vancomycin, 200 $\mu$/ml; cefotaxime, 500 $\mu g$/ml and is buffered to pH 5.7 with MES, 3 mM. Ten explants are washed in each petri dish with constant, slow gyratory agitation at room temperature for four days. Counterselection medium is replaced four times.

The explants are picked to agarose solidified selection medium. Selection medium consists of B5 salts (G5893), 3.2 gm/L; sucrose, 2.0% w/v; BAP, 5.0 $\mu M$; IBA, 0.5 $\mu M$; kanamycin sulfate, 50 $\mu g$/ml; vancomycin, 100 $\mu g$/ml; cefotaxime, 30 $\mu g$/ml; timentin, 30 $\mu g$/ml and is buffered to pH 5.7 with MES, 3.0 mM. Selection medium is solidified with SeaKem agarose, 0.3% w/v. The explants are embedded in the medium, adaxial side down and cultured at 28° C. with a 16 hour day length and cool white fluorescent light, of 60–80 $\mu Em^2S^1$.

After two weeks explants are washed with liquid medium on the gyratory shaker. This time the wash is conducted overnight in counterselection medium containing kanamycin sulfate, 50 $\mu g$/ml. The following day explants are picked to agarose solidified selection medium. Again they are embedded in the medium, adaxial side down, and cultured as before for another two weeks.

After one month on selective media, transformed tissue becomes visible as green sectors of regenerating tissue against a background of bleached, less healthy tissue. Explants without green sectors are discarded, explants with green sectors are transferred to elongation medium. Elongation medium consists of B5 salts (G5893), 3.2 gm/L; sucrose, 2.0% w/v; IBA, 3.3 $\mu M$; gibberellic acid, 1.7 $\mu M$; vancomycin, 100 $\mu g$/ml; cefotaxime, 30 $\mu g$/ml; timentin, 30 $\mu g$/ml and is buffered to pH 5.7 with MES, 3.0 mM. Elongation medium is solidified with gelrite, 0.2% w/v. Explants are embedded adaxial side up and cultured as before. Culture is continued on this medium with transfers to fresh plates every two weeks.

When shoots become 0.5 cm in length they are excised at the base and placed in rooting medium in 13×100 mm test tubes. Rooting medium consists of B5 salts (G5893), 3.2 gm/L; sucrose, 15 gm/L; nicotinic acid, 20 $\mu M$; pyroglutamic acid (PGA), 900 mg/L and IBA, 10 $\mu M$. The medium is buffered to pH 5.7 with MES, 3.0 mM and solidified with GelRite, 0.2% w/v. After ten days the shoots are transferred to the same medium without IBA or PGA. Shoots are rooted and held in these tubes under the same environmental conditions as before.

Once a root system is well established, the plantlet is transferred to sterile soil mix in plant cons (ICN Biomedicals, Inc.; Catalogue Nos. 26-720 and 1-02). Temperature, photoperiod and light intensity remain the same as before. Under these conditions the regenerates become vigorous, somewhat small, but mostly normal plants. When their root systems become well established, a corner of the plant con is cut off and the plants are gradually hardened off in an environmental chamber or greenhouse. Finally they are potted in solid mix and grown to maturity, bearing seed, in a greenhouse.

C. Analysis of Paraveinal Mesophyll Produced by Transgenic Plants

Mature paraveinal mesophyll from several independent transgenic lines containing the SFA-8 gene is extracted in 2× Laemmli buffer. Proteins are quantitated using a modified Lowry kit from Bio-Rad using bovine serum albumin as a standard. Equal amounts of protein are loaded onto 4–20% Tris-glycine polyacrylamide gels. Molecular weight standards in the range of 3–116 kD are obtained from Novex and run alongside the protein samples. Gels are run in duplicate with one being electrophoretically transferred to Immobilon PVDF membrane for western blotting and the other being used for Coomassie staining. Western blots were performed using affinity purified antibodies against the sunflower 2S albumin and the signal is detected by the Western-Light Chemiluminescent Detection System from Tropix, Inc. (Bedford, Mass.) as per the manufacture's instructions.

Total amino acid composition can be determined by acid hydrolysis of tobacco or soybean meal by standard protocols. Seed proteins also can be analyzed for trypsin inhibitor activity according to the previously described protocols of Kollipara, et al., *J. Agricul. Food Chem.*; Vol. 40; pp. 2356; (1992); incorporated herein in its entirety by reference. Similarly chymotrypsin inhibitory assays can be done according to Geiger, Chymotrypsin. In "Methods of Enzymatic Analysis," pp. 99–109; (1984); incorporated herein in its entirety by reference.

II. Expression of Sunflower cDNA in Soybean Seed

A) Creation of Expression Vector that Contains Sulfur-rich Sunflower 2S Albumin

A full-length cDNA clone for the sunflower SFA-8 protein is obtained using RT-PCR with first strand cDNA as template and gene-specific primers designed against published sequences. See Matsumura, et al., and Lilley, et al., supra. The resulting PCR products are subcloned into pBluescript SKII and confirmed by sequence analysis. The genes are transferred into p4752, which contains the 5' and 3' regulatory sequences from phaseolin. Sengupta-Gopalan et al., *Proc. Nat'l. Acad. Sci.*; Vol. 82; p. 3320; (1985); incorporated herein in its entirety by reference. The resulting expression cassettes contain SFA-8 under control of the phaseolin regulatory sequences. This plasmid is then ligated back to itself to produce a construct which contains tandem repeats of the expression cassettes. A final set of ligations is performed to generate p7518 a construct which contains four tandem copies of the expression cassette.

The construct containing the four tandem copies is then transferred to the binary vector pARC12, a vector which contains the NPTII selectable marker for plant selection. This vector is transformed into *Agrobacterium tumefaciens* strain LBA4404 by a freeze-thaw method (*Plant Molecular Biology*, op cit.), and presence of a complete copy of the 4× construct is confirmed.

B) Explant Preparation, Transformation and Transgenic Plant Recovery

Seeds of soybean (*Glycine max*), var. PHI9341, are surface sterilized by exposure to chlorine gas evolved in a glass bell jar. Gas is produced by adding 3.5 ml hydrochloric acid (34–37% w/w). Exposure is for 16–20 hours in a container approximately one cubic foot in volume. Surface sterilized seed is stored in petri dishes at room temperature. Seed is germinated by plating of 1/10 strength agar solidified medium according to Gamborg (B5 basal medium with minimal organics, Sigma Chemical co., Cat. No. G5893, 0.32 gm/L; sucrose, 0.2% w/v and 2-[N-morpholino] ethanesulfonic acid] (MES), 3.0 mM without plant growth regulators and culturing at 28° C. with a 16 hour day length and cool white fluorescent illumination of approximately 20 $\mu Em^2S^1$. After three or four days, seed is prepared for co-cultivation. The seed coat is removed and the elongating radical is removed 3-4 mm below the cotyledons. Ten prepared seed are held in each of several petri dishes.

Overnight cultures of A. tumefaciens LBA4404 harboring the expression construct, are grown to log phase in Minimal A medium containing tetracycline, 1.0 $\mu$g/ml. Cultures are pooled and an optical density at 550 nm is measured. An amount of culture sufficient to collect upon sedimentation between 1.0 and $2.0 \times 10^{10}$ cells, where O.D. 550 1.0=1.4× $10^9$ cells/ml, is placed in a 15 ml conical centrifuge tube and spun down at 6000 g for 10 minutes. After centrifugation the supernatant is decanted and the tubes are held at room temperature until inoculum is needed, but not longer than one hour.

Inoculations are conducted in batches such that each plate of seed is treated with a newly resuspended pellet of A. tumefaciens harboring the 4x construct. One at a time the pellets are resuspended in 20 ml inoculation medium. Inoculation medium consists of B5 salts (B5893), 3.2 gm/L; sucrose, 2.0% w/v; BAP, 44 $\mu$M; and indolebutyric acid (IBA), 0.5 $\mu$M. Acetosyringone (AS), 100 $\mu$M is added and the medium is buffered to pH 5.5 with MES, 10 mM.

The mixture is resuspended by vortexing and the inoculum is poured into a petri dish containing prepared seed and the cotyledonary nodes are macerated with a surgical blade. This is accomplished by dividing seed in half by longitudinal section through the shoot apex, preserving the two whole cotyledons. The two halves of the shoot apex are broken off at their respective cotyledons by prying them away with a surgical blade. The cotyledonary node is then macerated with the surgical blade by repeated scoring along the axis of symmetry. Care is taken not to cut entirely through the explant to the adaxial side. Twenty explants are prepared in roughly five minutes and then incubated for 30 minutes at room temperature without agitation. Additional plates are prepared during this time. After 30 minutes the explants are transferred to plates of the same medium solidified with Gelrite (Merck & Co., Inc.), 0.2% w/v. Explants are embedded with the adaxial side up and level with the surface of the medium and cultured at 22° C. for three days under cool white fluorescent light. Approximately 20 $\mu Em^2S^1$.

After three days the explants are moved to liquid counterselection medium. Counterselection medium consists of B4 salts (G5893), 3.2 gm/L; sucrose, 2.0% w/v; BAP, 5.0 $\mu$M; IBA, 0.5 $\mu$M; vancomycin, 200 $\mu$/ml; cefotaxime, 500 $\mu$g/ml and is buffered to pH 5.7 with MES, 3 mM. Ten explants are washed in each petri dish with constant, slow gyratory agitation at room temperature for four days. Counterselection medium is replaced four times.

The explants are picked to agarose solidified selection medium. Selection medium consists of B5 salts (G5893), 3.2 gm/L; sucrose, 2.0% w/v; BAP, 5.0 $\mu$M; IBA, 0.5 $\mu$M; kanamycin sulfate, 50 $\mu$g/ml; vancomycin, 100 $\mu$g/ml; cefotaxime, 30 $\mu$g/ml; timentin, 30 $\mu$g/ml and is buffered to pH 5.7 with MES, 3.0 mM. Selection medium is solidified with SeaKem agarose, 0.3% w/v. The explants are embedded in the medium, adaxial side down and cultured at 28° C. with a 16 hour day length and cool white fluorescent light, of 60-80 $\mu Em^2S^1$.

After two weeks explants are washed with liquid medium on the gyratory shaker. This time the wash is conducted overnight in counterselection medium containing kanamycin sulfate, 50 $\mu$g/ml. The following day explants are picked to agarose solidified selection medium. Again they are embedded in the medium, adaxial side down, and cultured as before for another two weeks.

After one month on selective media, transformed tissue becomes visible as green sectors of regenerating tissue against a background of bleached, less healthy tissue. Explants without green sectors are discarded, explants with green sectors are transferred to elongation medium. Elongation medium consists of B5 salts (G5893), 3.2 gm/L; sucrose, 2.0% w/v; IBA, 3.3 $\mu$M; gibberellic acid, 1.7 $\mu$M; vancomycin, 100 $\mu$g/ml; cefotaxime, 30 $\mu$g/ml; timentin, 30 $\mu$g/ml and is buffered to pH 5.7 with MES, 3.0 mM. Elongation medium is solidified with gelrite, 0.2% w/v. Explants are embedded adaxial side up and culture as before. Culture is continued on this medium with transfers to fresh plates every two weeks.

When shoots become 0.5 cm in length they are excised at the base and placed in rooting medium in 13×100 mm test tubes. Rooting medium consists of B5 salts (G5893), 3.2 gm/L; sucrose, 15 gm/L; nicotinic acid, 20 $\mu$M; pyroglutamic acid (PGA), 900 mg/L and IBA, 10 $\mu$M. The medium is buffered to pH 5.7 with MES, 3.0 mM and solidified with GelRite, 0.2% w/v. After ten days the shoots are transferred to the same medium without IBA or PGA. Shoots are rooted and held in these tubes under the same environmental conditions as before.

Once a root system is well established, the plantlet is transferred to sterile soil mix in plant cons (ICN Biomedicals, Inc.; Catalogue Nos. 26-720 and 1-02). Temperature, photoperiod and light intensity remain the same as before. Under these conditions the regenerates become vigorous, somewhat small, but mostly normal plants. When their root systems become well established, a corner of the plant con is cut off and the plants are gradually hardened off in an environmental chamber or greenhouse. Finally they are potted in solid mix and grown to maturity, bearing seed, in a greenhouse.

C) Analysis of Seeds Produced by Transgenic Plants

Mature seed from several independent transgenic lines containing the SFA-8 gene is extracted in 2x Laemmli buffer. Proteins are quantitated using a modified Lowry kit from Bio-Rad using bovine serum albumin as a standard. Equal amounts of protein are loaded onto 4–20% Trisglycine polyacrylamide gels. Molecular weight standards in the range of 3–116 kD are obtained from Novex and run alongside the protein samples. Gels are run in duplicate with one being electrophoretically transferred to Immobilon PVDF membrane for western blotting and the other being used for Coomassie staining. Western blots were performed using affinity purified antibodies against the sunflower 2S albumin and the signal is detected by the Western-Light Chemiluminescent Detection System from Tropix, Inc. (Bedford, Mass.) as per the manufacture's instructions.

Total amino acid composition can be determined by acid hydrolysis of tobacco or soybean meal by standard protocols. Seed proteins also can be analyzed for trypsin inhibitor activity according to the previously described protocols of Kollipara et al., *J. Agricul. Food Chem.*; Vol. 40; pp. 2356; (1992); incorporated herein in its entirety by reference. Similarly chymotrypsin inhibitory assays can be done according to Geiger, Chymotrypsin. In "Methods of Enzymatic Analysis," pp. 99–109;(1984); incorporated herein in its entirety by reference.

III. Expression of Engineered High-Lysine, Alpha-Hordothionine in Maize Photosynthetic Organs A) Construction of Expression Vector Standard molecular biology methods are used to make the sequence. A genomic clone containing the chlorophyll a/b binding protein has been published. A high lysine derivative of alpha-hordothionine is engineered having the sequence indicated in Sequence I.D. No. 1 by using published techniques. See WO 94,16078, incorporated herein in its entirety by reference. Additionally, this gene is engineered to contain an endoplasmic reticulum-targeting signal, KDEL, at the carboxy-terminus to enhance protein stability. See Wandelt, et al., "Vicilin with Carboxy-terminal KDEL is Retained in the Endoplasmic Reticulum and Accumulates to High Levels in the Leaves of Transgenic Plants," *The Plant Journal*, Vol. 2(2); pp. 181–192; (1992), incorporated herein in its entirety by reference. PINII, a 3' polyadenylation termination sequence has been published. The 3' end of the chlorophyll a/b binding protein promoter sequence is fused to the 5' end of the engineered alpha-hordothionine gene containing the KDEL sequence, and the 3' end of this fusion is fused to the 5' end of PINII. This expression construct, which contains the chlorophyll a/b binding protein promoter sequence, the engineered alpha-hordothionine gene containing the KDEL sequence, and the PINII termination signal is then transferred to the binary vector pARC12. The resulting vector is transformed into *Agrobacterium tumefaciens* strain LBA4404 by a freeze-thaw method and presence of a complete copy of the construct is confirmed.

In a preferred embodiment, a second alpha-hordothionine gene, as above, is targeted to the seed as described in Example II.

B) Transformation of Maize with the Alpha-Hordothionine Gene

The gene is transformed into embryogenic maize callus by particle bombardment. Transgenic maize plants are produced by bombardment of embryogenically responsive immature embryos with tungsten particles associated with DNA plasmids. The plasmids consist of a selectable and an unselectable marker gene.

C) Preparation of Tissue

Immature embryos of maize variety High Type II are the target for particle bombardment-mediated transformation. This genotype is the $F_1$ of two purebred genetic lines, parents A and B, derived from the cross of two known maize inbreds, A188 and B73. Both parents are selected for high competence of somatic embryogenesis, according to Armstrong et al., *Maize Genetics Coop. News*; Vol. 65; p. 92; (1991); incorporated herein in its entirety by reference.

Ears from $F_1$ plants are selfed or sibbed, and embryos are aseptically dissected from developing caryopses when the scutellum first became opaque. This stage occurs about 9–13 days post-pollination, and most generally about 10 days post-pollination, depending on growth conditions. The embryos are about 0.75 to 1.5 millimeters long. Ears are surface sterilized with 20–50% Clorox for 30 minutes, followed by three rinses with sterile distilled water.

Immature embryos are cultured with the scutellum oriented upward, on embyrogenic induction medium comprised of N6 basal salts, Eriksson vitamins, 0.5 mg/l thiamine HCL, 30 mg/l sucrose, 2.88 gm/l L-proline, 1 mg/l 2,4-dichlorophenoxyacetic acid, 2 gm/l Gelrite, and 8.5 mg/l $AgNo_3$. Chu, et al., *Sci. Sin.*; Vol. 18; p. 659; (1975); and Eriksson, *Physiol. Plant*; Vol. 18; p. 976; (1965); both incorporated herein in its entirety by reference. The medium is sterilized by autoclaving at 121° C. for 15 minutes and dispensed into 100×25 mm petri dishes. $AgNO_3$ is filter-sterilized and added to the medium after autoclaving. The tissues are cultured in complete darkness at 28° C. After about 3 to 7 days, most usually about 4 days, the scutellum of the embryo swells to about double its original size and the protuberances at the coleorhizal surface of the scutellum indicate the inception of embryogenic tissue. Up to 100% of the embryos can display this response, but most commonly, the embryogenic response frequency was about 80%.

When the embryogenic response is observed, the embryos are transferred to a medium comprised of induction medium modified to contain 120 gm/l sucrose. The embryos are oriented with the coleorhizal pole, the embryogenetically responsive tissue, upwards form the culture medium. Ten embryos per petri dish are located in the center of a petri dish in an area about 2 cm in diameter. The embryos are maintained on this medium for 3–16 hours, preferably 4 hours, in complete darkness at 28° C. just prior to bombardment with particles associated with plasmid DNAs containing the selectable and unselectable marker genes.

To effect particle bombardment of embryos, the particle-DNA agglomerates are accelerated using a DuPont PDS-1000 particle acceleration device. The particle-DNA agglomeration is briefly sonicated and 10 μl are deposited on macrocarriers and the ethanol is allowed to evaporate. The macrocarrier is accelerated onto a stainless-steel stopping screen by the rupture of a polymer diaphragm (rupture disk). Rupture is effected by pressurized helium. The velocity of particle-DNA acceleration is determined based on the rupture disk breaking pressure. Rupture disk pressures of 200 to 1800 psi are used, with 650 to 1100 psi being preferred, and about 900 psi being most highly preferred. Multiple disks are used to effect a range of rupture pressures.

The shelf containing the plate with embryos is placed 5.1 cm below the bottom of the macrocarrier platform (shelf #3). To effect particle bombardment of cultured immature embryos, a rupture disk and a macrocarrier with dried particle-DNA agglomerates are installed in the device. The He pressure delivered to the device is adjusted to 200 psi above the rupture disk breaking pressure. A petri dish with the target embryos is placed into the vacuum chamber and located in the projected path of accelerated particles. A vacuum is created in the chamber, preferably about 28 in Hg. After operation of the device, the vacuum is released and the petri dish is removed.

Bombarded embryos remain on the osmotically-adjusted medium during bombardment, and 1 to 4 days subsequently. The embryos are transferred to selection medium comprised of N6 basal salts, Eriksson vitamins, 0.5 mg/l thiamine HCL, 30 gm/l sucrose, 1 mg/l 2,4-dichlorophenoxyacetic acid, 2 gm/l Gelrite, 0.85 mg/l Ag $NO_3$ and 3 mg/l bialaphos (Herbiace, Meiji). Bialaphos is added filter-sterilized. The embryos are subcultured to fresh selection medium at 10 to 14 day intervals. After about 7 weeks, embryogenic tissue, putatively transformed for both selectable and unselected marker genes, proliferate from about 7% of the bombarded embryos. Putative transgenic tissue is rescued, and that tissue derived from individual embryos was considered to be an event and is propagated independently on selection medium. Two cycles of clonal propagation are achieved by visual selection for the smallest contiguous fragments of organized embryogenic tissue.

A sample of tissue from each event is processed to recover DNA. The DNA is restricted with a restriction endonuclease and probed with primer sequences designed to amplify DNA sequences overlapping the alpha-hordothionine and non alpha-hordothionine portion of the plasmid. Embryogenic tissue with amplifiable sequence is advanced to plant regeneration.

For regeneration of transgenic plants, embryogenic tissue is subcultured to a medium comprising MS salts and vitamins (Murashinge & Skoog, *Physiol. Plant*; Vol. 15; p. 473; (1962); incorporated herein in its entirety by reference), 100 mg/l myo-inositol, 60 gm/l sucrose, 3 gm/l Gelrite, 0.5 mg/l zeatin, 1 mg/l indole-3-acetic acid, 26.4 ng/l ±cis-trans-abscissic acid, and 3 mg/l bialaphos in 100×25 mm petri dishes, and is incubated in darkness at 28° C. until the development of well-formed, matured somatic embryos could be seen. This requires about 14 days. Well-formed somatic embryos are opaque and cream-colored, and are comprised of an identifiable scutellum and coleoptile. The embryos are individually subcultured to a germination medium comprising MS salts and vitamins, 100 mg/l myo-inositol, 40 mg/l sucrose and 1.5 gm/l Gelrite in 100×25 mm petri dishes and incubated under a 16 hour light: 8 hour dark photoperiod and 40 $\mu Em^2S^1$ from cool-white fluorescent rubes. After about 7 days, the somatic embryos germinate and produce a well-defined shoot and root. The individual plants are subcultured to germination medium in 125×25 mm glass tubes to allow further plant development. The plants are maintained under a 16 hour light:8 hour dark photoperiod and 40 $\mu einsteinsm^{-2}sec^{-1}$ from cool-white fluorescent tubes. After about 7 days, the plants are well-established and are transplanted to horticultural soil, hardened off, and potted into commercial greenhouse soil mixture and grown to sexual maturity in a greenhouse. An elite inbred line is used as a male to pollinate regenerated transgenic plants.

D) Preparation of Particles

Fifteen mgs of tungsten particles (General Electric), 0.5 to 1.8 $\mu$, preferably 1 to 1.8 $\mu$, and most preferably 1 $\mu$, are added to 2 mls of concentrated nitric acid. This suspension is sonicated at 0° C. for 20 minutes (Branson Sonifier Model 450, 40% output, constant duty cycle). Tungsten particles were pelleted by centrifugation at 10000 rpm (Biofuge) for one minute, and the supernatant is removed. Two mls of sterile distilled water are added to the pellet, and brief sonication is used to resuspend the particles. The suspension is pelleted, one ml of absolute ethanol is added to the pellet, and brief sonication is used to resuspend the particles. Rinsing, pelleting, and resuspending of the particles is performed two more times with sterile distilled water, and finally the particles are resuspended in two mls of sterile distilled water. The particles are subdivided into 250-$\mu$l aliquots and stored frozen.

E) Preparation of Particle-Plasmid DNA Association

The stock of tungsten particles is sonicated briefly in a water bath sonicator (Branson Sonifier Model 450, 20% output, constant duty cycle) and 50 $\mu$l is transferred to a microfuge tube. Equimolar amounts of selectable and unselectable plasmid DNA are added to the particles for a final DNA amount of 0.1 to 10 $\mu$g in 10 $\mu$l total volume, and briefly sonicated. Preferably, 1 $\mu$g total DNA is used. Specifically, 3.5 $\mu$l of $ubi_P$:ubiint::BAR::PinII$_1$, plus 6.5 $\mu$l of Cab::HT12::PinII, both at 0.1 $\mu$g/$\mu$l in TE buffer, are added to the particle suspension. Fifty microliters of sterile aqueous 2.5 M $CaCl_2$ are added, and the mixture is briefly sonicated and vortexed. Twenty microliters of sterile aqueous 0.1 M spermidine are added and the mixture is briefly sonicated and vortexed. The mixture is incubated at room temperature for 20 minutes with intermittent brief sonication. The particle suspension is centrifuged, and the supernatant is removed. Two hundred fifty microliters of absolute ethanol are added to the pellet, followed by brief sonication. The suspension is pelleted, the supernatant is removed, and 60 $\mu$l of absolute ethanol are added. The suspension is sonicated briefly before loading the particle-DNA agglomeration onto macrocarriers.

F) Extraction and Characterization of Protein from Transgenic Leaves and Seed

Transgenic leaves thus obtained are extracted and characterized according to methods described in Example I c). To extract and characterize protein from transgenic seed, embryos are hand-dissected from dry, mature kernels sampled from fully developed ears and endosperms are pulverized to a fine meal with a ball mill. Alpha-zeins are extracted overnight in 70% (v/v) ethanol with constant shaking at 37° C. After centrifugation for 15 minutes at 12,000 rpm, the supernatant is collected, vacuum dried, and stored at 4° C. until use. Total zeins and non-zein proteins are isolated according to Wallace et al., *Plant Physiol.*; Vol. 92; pp. 191–196; (1990); incorporated herein in its entirety by reference.

SDS-polyacrylamide gels (10 and 12.5%, w/v) and gradient gels (7.5–18%, w/v) are prepared according to Laemmli, *Nature*, Vol. 227; pp. 680–685; (1970); incorporated herein in its entirety by reference, but the TRIS concentrations used in the resolving gel and running buffer are doubled. Protein samples are diluted in Laemmli sample buffer and boiled for 3 minutes before loading. Gradient and 12.5% gels are run at room temperature at a constant current until the dye front migrated through the stacking gel, and then at 250 mA through the resolving gel. Gels are stained with Coomassie overnight, and destined in 40% (v/v) methanol and 10% (v/v) acetic acid for at least 8 hours. Immunoblotting analyses are used specifically to detect α-zeins in protein extracts. Protein extracts are separated by SDS-PAGE as described above, transferred to nitrocellulose filters, and treated with a rabbit anti-polyclonal antibody. Lending, et al., *Protoplasma*; Vol. 143; pp. 51–62; (1988); incorporated herein in its entirety by reference. Goat anti-rabbit alkaline phosphatase conjugate is used for indirect detection, as described by Knecht, et al., *Anal. Biochem.*; Vol. 136; pp. 180–184; (1984); incorporated herein in its entirety by reference.

The foregoing is one description of the scope of the invention and a skilled artisan will recognize many other examples of plant improvement to which the invention can be applied.

What is claimed is:

1. A seed-crop plant, genetically modified by the steps comprising:
   a) expressing a transgene in an organ or tissue of a plant other than the seed, wherein the transgene encodes an amino acid sequence enriched in a target amino acid; and
   b) accumulating the target amino acid in the seed to a level greater than in the wild type seed.

2. A plant according to claim 1 wherein the amino acid is selected from the group consisting of alanine, asparagine, aspartate, cysteine, glutamate, glutamine, glycine, proline, serine, tyrosine, arginine, histidine, isoleucine, leucine, lysine, methionine, phenylalanine, threonine, tryptophan, and valine.

3. A plant according to claim 2 wherein the amino acid is selected from the group consisting of arginine, histidine, isoleucine, leucine, lysine, methionine, cysteine, phenylalanine, threonine, tryptophan and valine.

4. A plant according to claim 3 wherein the plant is selected from the group consisting of soybean, canola, corn, sunflower, wheat, barley, oats, millet, rice, sorghum and rye.

5. A plant according to claim 1 wherein the amino acid sequence is a protein.

6. A plant according to claim 5 wherein the protein is a storage protein.

7. A plant according to claim 1 wherein the first transgene is expressed in the root, leaf, stem, pod, mesophyll, palisade, cortex, bundle sheath, paraveinal mesophyll or epidermis.

8. A plant according to claim 1 wherein the expression of the transgene is under the control of a promoter selected from the group consisting of vspA, vspB, rubisco activase, ferredoxin, rubisco small subunit and chlorophyll AB binding protein.

9. A plant according to claim 1 wherein the genetic modification further comprises the step of expressing a second transgene in the seed which encodes a protein enriched in the target amino acid.

10. A plant according to claim 9 wherein the protein contains at least 20% more target amino acid than the average protein.

11. A plant according to claim 10 wherein the protein contains at least 50% more target amino acid than the average protein.

12. A plant according to claim 11 wherein the protein is a storage protein.

13. A plant according to claim 12 wherein the protein is a seed storage protein.

14. A plant according to claim 13 wherein the protein is selected from the group consisting of rice 10 kDa, 13 kDa and 16 kDa promaline; sunflower 2S albumin protein; Brazil nut 2S albumin protein; soybean seed storage protein; 10 kDa zein protein; thionin; 2S albumin from alfalfa and soybean albumin.

15. A plant according to claim 14 wherein the protein is sunflower albumin-8 or a high lysine derivative of alpha-hordothionin.

16. A plant according to claim 9 wherein the expression of the second transgene is under the control of a promoter selected from the group consisting of the β-conglycinin, β-phaseolin, napin, soybean lectin, maize 15 kD zein, 22 kD zein, γ-zein, waxy, shrunken 1, globulin 1 and shrunken 2.

17. A plant according to claim 9 which is soybean or corn.

18. A plant according to claim 17 which is a soybean plant and the protein is sunflower albumin-8.

19. A plant according to claim 17 which is a corn plant and the protein is a high lysine derivative of alpha-hordothionin.

20. A seed produced by the plant of claim 1.

21. A seed produced by the plant of claim 9.

22. A seed produced by the plant of claim 4.

* * * * *

SEQUENCE LISTING (1) GENERAL INFORMATION:

(iii) NUMBER OF SEQUENCES: 1

(2) INFORMATION FOR SEQ ID NO: 1:

```
    (i) SEQUENCE CHARACTERISTICS:
        (A) LENGTH: 45 amino acids
        (B) TYPE: amino acid
        (C) STRANDEDNESS: single
        (D) TOPOLOGY: linear (ii) MOLECULE TYPE: protein
        (A) DESCRIPTION: hordothionin derivative (xi) SEQUENCE DESCRIPTION: SEQ ID NO: 1:

Lys Ser Cys Cys Lys Ser Thr Leu Gly Arg
                 5                  10

Lys Cys Tyr Asn Leu Cys Lys Val Lys Gly
                15                  20

Ala Lys Lys Leu Cys Ala Gly Val Cys Lys
                25                  30

Cys Lys Leu Thr Ser Ser Gly Lys Cys Pro
                35                  40

Lys Gly Phe Pro Lys
                45
```